United States Patent [19]
Saito et al.

[11] Patent Number: 5,824,822
[45] Date of Patent: Oct. 20, 1998

[54] PHOSPPHINE-PHOSINITE COMPOUND AND PROCESS FOR PREPARING 4-[(R)-1'-FORMYLETHYL]-AZETIDIN-2-ONE DERIVATIVES USING THE SAME

[75] Inventors: Takao Saito, Kanagawa; Akifumi Yoshida, Shizuoka; Kazuhiko Matsumura, Kanagawa; Takashi Miura, Kanagawa; Hidenori Kumobayashi, Kanagawa, all of Japan

[73] Assignee: Takasago International Corporation, Tokyo, Japan

[21] Appl. No.: 677,226

[22] Filed: Jul. 9, 1996

[30] Foreign Application Priority Data

Jul. 27, 1995 [JP] Japan .................................. 7-210215

[51] Int. Cl.⁶ ............................. C07F 9/02; C07D 205/00
[52] U.S. Cl. ................................. 568/10; 568/14; 540/200
[58] Field of Search ...................... 568/10, 14; 540/200

[56] References Cited

U.S. PATENT DOCUMENTS 5,530,150  6/1996  Takaya et al. ............................. 556/18

FOREIGN PATENT DOCUMENTS 0 614 903 A2  9/1994  European Pat. Off. .......... C07F 9/50
6-316560    11/1994  Japan .......................... C07D 205/08

OTHER PUBLICATIONS

Tolman C.A., "Electron Donor—Acceptor . . . ", J. Amer. Chem. Soc., vol. 92(10), May 20, 1970, pp. 2953–2956.

Tolman C.A., "Phosphorus Liggand Exchange . . . ", J. Amer. Chem. Soc., vol. 92(10), May 20, 1970, pp. 2956–2965.

Tolman C.A., "Steric Effects of Phosphorus . . . ", Chemical Reviews, vol. 77(3), 1977, pp. 313–348.

Hobbs et al, *Asymmetric Hydroformylation of Vinyl Acetate with DIOP–Type Ligands*, 1981, pp. 4422–4427.

Hayashi et al, *Catalytic Hydroformylation by th Use of Rhodium–complexes of Chiral Bidentate Phosphorus Ligands Bearing Saturated Ring Skeletons*, Sep. 1979 vol. 52 pp. 2605–2608.

Gladiali et al, *Completely Regioselective Hydroformylation of Methyl N–Acetamidoacrylate by Chiral Rhodium Phosphine Catalysts*, 1990, vol. 1, No. 10 pp. 693–696.

Sakai et al, *Asymmetric Hydroformylation of Vinyl Acetate By Use of Chiral Bis*(triarylphosphite) *Rhodium*(I)*Complexes*, 1992, vol. 3 No. 5 pp. 583–586.

Sakai et al, *Highly Enantioselective Hydroformylation of Olefins Catalyzed by New Phosphinephosphite–Rh(I) Complexes*, 1993, pp. 7033–7034.

*Primary Examiner*—Mukund J. Shah
*Assistant Examiner*—Tamthom T. Ngo
*Attorney, Agent, or Firm*—Sughrue, Mion, Zinn, Macpeak & Seas, PLLC

[57] ABSTRACT

A phosphine-phosphinite compound represented by formula (I):

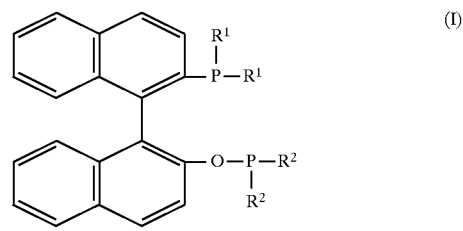

wherein $R^1$ and $R^2$, which may be the same or different, each represent a substituted or unsubstituted phenyl group or a substituted or unsubstituted naphthyl group, and a process for preparing a 4-[(R)-1'-formylethyl]azetidin-2-one derivative using the compound (I). The compound (I), either in combination, or as a complex, with a transition metal compound, is useful as a catalyst for asymmetric hydroformylation and makes it possible to easily synthesize an important intermediate for carbapenem antibiotics or a precursor thereof at high regioselectivity and diastereoselectivity.

3 Claims, No Drawings

PHOSPPHINE-PHOSINITE COMPOUND AND PROCESS FOR PREPARING 4-[(R)-1'-FORMYLETHYL]-AZETIDIN-2-ONE DERIVATIVES USING THE SAME

FIELD OF THE INVENTION

This invention relates to a novel phosphine-phosphinite compound and a process for preparing an optically active aldehyde compound by using the phosphine-phosphinite compound as a catalyst. More particularly, it relates to a phosphine-phosphinite compound which is combined with a rhodium compound to serve as a useful catalyst for asymmetric hydroformylation, and to a process for preparing a 4-[(R)-1'-formylethyl]azetidin-2-one derivative, an important intermediate of antibiotics, by using the phosphine-phosphinite compound as a catalyst component.

BACKGROUND OF THE INVENTION

A number of transition metal catalysts have been used in catalyst systems for organic syntheses. In particular, noble metal complexes, though expensive, have been given much study for their applicability to syntheses as a catalyst because of their stability and ease of handling, and have made it feasible to achieve organic syntheses reactions that had been deemed impossible with traditional techniques.

In particular, complexes of a transition metal, e.g., rhodium or ruthenium, having an optically active tertiary phosphine ligand coordinated thereto are known to be excellent catalysts for asymmetric syntheses. In order to further enhance the performance of these complex catalysts, a great variety of phosphine compounds having a specific structure have been developed to date (see The Chemical Society of Japan (ed.), *Kagaku Sosetsu* 32, "Yuki Kinzoku no Kagaku", pp. 237–238 (1982)).

Attention being paid to, for instance, asymmetric hydroformylation using a transition metal-phosphine complex, *J. Org. Chem.*, Vol. 46, p. 4422 (1981) teaches a reaction using a rhodium complex having optically active 2,3-o-diisopropylidene-2,3-dihydroxy-1,4-bis(diphenylphosphino)butane (hereinafter abbreviated to DIOP) as a ligand; *Bull. Chem. Soc. Jpn.*, Vol. 52, p. 2605 (1976) reports a reaction using a rhodium complex having an optically active bidentate phosphine ligand (e.g., DIOP); and *Tetrahedron Asymmetry*, Vol. 10, p. 693 (1990) describes the use of a rhodium complex having DIOP, etc., in the catalytic asymmetric hydroformylation of methyl acetamidoacrylate.

On the other hand, known complex catalysts having an optically active tertiary phosphite ligand include ones having an optically active bis(triarylphosphite) ligand having a binaphthyl skeleton as disclosed in *Tetrahedron Asymmetry*, Vol. 3, p. 583 (1992), in which asymmetric hydroformylation of vinyl acetate using a rhodium catalyst having the above ligand is reported.

In recent years, it was reported that a ligand having a binaphthyl skeleton and yet having an asymmetric structure with no $C_2$ chirality, designated BINAPHOS, is useful in the asymmetric hydroformylation of olefins (see *J. Am. Chem. Soc.*, Vol. 115, p. 7033 (1993)).

While various catalysts have thus been proposed for asymmetric syntheses, further increased selectivity is often required for some desired compounds. It has therefore been demanded to develop a high performance catalyst system meeting the demand.

High selectivity is demanded especially in the medical field. For example, JP-A-6-316560 (the term "JP-A" as used herein means an "unexamined published Japanese patent application") discloses a process for preparing a 4-[(R)-1'-formylethyl]azetidin-2-one derivative represented by formula (III):

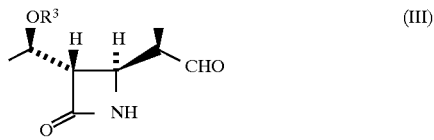

wherein $R^3$ represents a hydrogen atom or a protective group for a hydroxyl group. The compound of formula (III) is an important intermediate for carbapenem antibiotics which have recently been given active studies. The above process comprises hydroformylating a 4-vinylazetidin-2-one compound using, as a catalyst, a metal compound, such as a rhodium compound, and a phosphine compound represented by the formula:

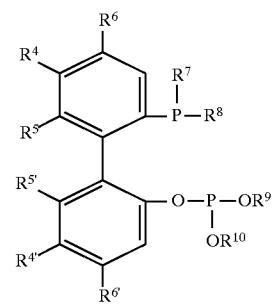

wherein $R^5$ and $R^{5'}$, which may be the same or different, each represent a hydrogen atom, a lower alkyl group or a lower alkoxy group; $R^4$, $R^{4'}$, $R^6$, and $R^{6'}$, which may be the same or different, each represent a hydrogen atom, a lower alkyl group, a lower alkoxy group or a halogen atom, or $R^4$ and $R^5$ or $R^{4'}$ and $R^{5'}$ are taken together to form a ring; $R^7$ and $R^8$, which may be the same or different, each represent a phenyl group which may be substituted with a lower alkyl group, a halogen atom or a lower alkoxy group; and $R^9$ and $R^{10}$, which may be the same or different, each represent a phenyl group which may be substituted with a lower alkyl group, a lower alkoxy group or a halogen atom, or $R^9$ and $R^{10}$ are taken together to form a divalent hydrocarbon group.

It is known that the above hydroformylation reaction involves the formation of not only a desired β-form or (R)-form but a considerable proportion of an n-form, which is a by-product attributed to the positional selectivity in bonding a formyl group, and an a-form (i.e., an (S)-form), which is attributed to the directional selectivity in bonding a formyl group and is reflected by the optical yield of the product, as illustrated in the following scheme:

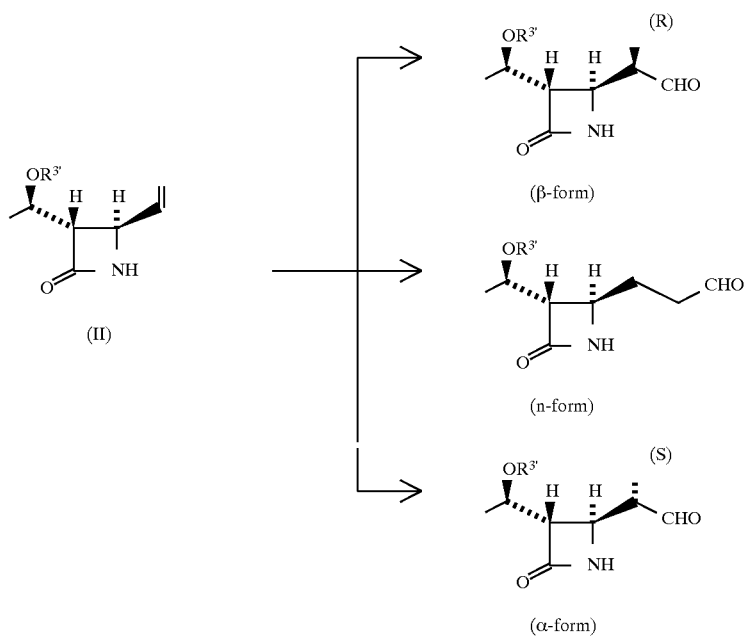

wherein R³' represents a t-butyldimethylsilyl group. It has therefore been demanded to develop a catalyst system for the above reaction which attains the desired positional selectivity and a high optical yield and thereby provides a desired product in high yield.

As described above, although a large number of optically active phosphine compounds have hitherto been developed as a catalyst component for asymmetric hydroformylation, they are sometimes unsatisfactory in regioselectivity, catalytic activity, and optical yield depending on the substrate of hydroformylation. It has therefore been demanded to develop a novel phosphine ligand which provides a catalyst system achieving a higher regioselectivity and a higher optical yield than conventional catalysts. It has been particularly desired to establish a process for preparing the above-mentioned compound (III) having a methyl group in the β-configuration, which is of high utility as an important intermediate for carbapenem antibiotics, at high selectivity and high efficiency.

SUMMARY OF THE INVENTION

An object of the invention is to provide a novel phosphine-phosphinite compound which exhibits higher catalyst performance.

Another object of the invention is to provide a process for preparing a 4-[(R)-1'-formylethyl]azetidin-2-one derivative of formula (III) at high selectivity and high efficiency.

As a result of extensive investigations, the inventors have found that a phosphine-phosphinite compound represented by formula (I):

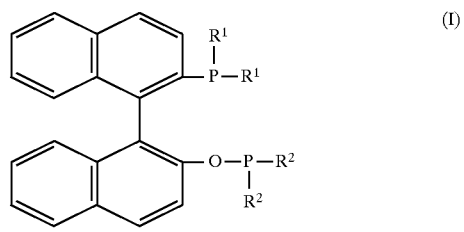

wherein R¹ and R², which may be the same or different, each represent a phenyl group; a phenyl group substituted with a lower alkyl group, a lower alkoxy group, a phenyl group, a halogen atom, a halogen-substituted lower alkyl group, a lower alkyl-substituted phenyl group, a tri(lower alkyl)silyl group, a cyclopentyl group, a 3,4-methylenedioxy group or a 3,4-ethylenedioxy group, a naphthyl group, or a naphthyl group substituted with a lower alkyl group, a lower alkoxy group or a halogen atom, contributes to selectivity in hydroformylation; and that application of the form of the phosphine-phosphinite compound (I) to hydroformylation of a 4-vinylazetidin-2-one compound (II):

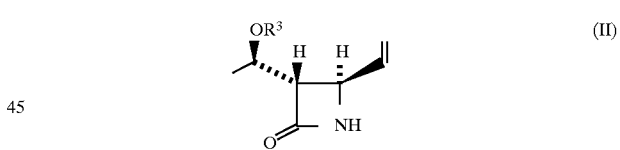

wherein R³ is as defined above, makes it possible to increase both a desired regioselectivity in bonding a formyl group and a diastereo-selectivity in bonding a formyl group (i.e., optical yield), thereby producing a compound (III) having a methyl group with β-configuration.

DETAILED DESCRIPTION OF THE INVENTION

The phosphine-phosphinite compound according to the invention can be obtained through, for example, the following reaction scheme:

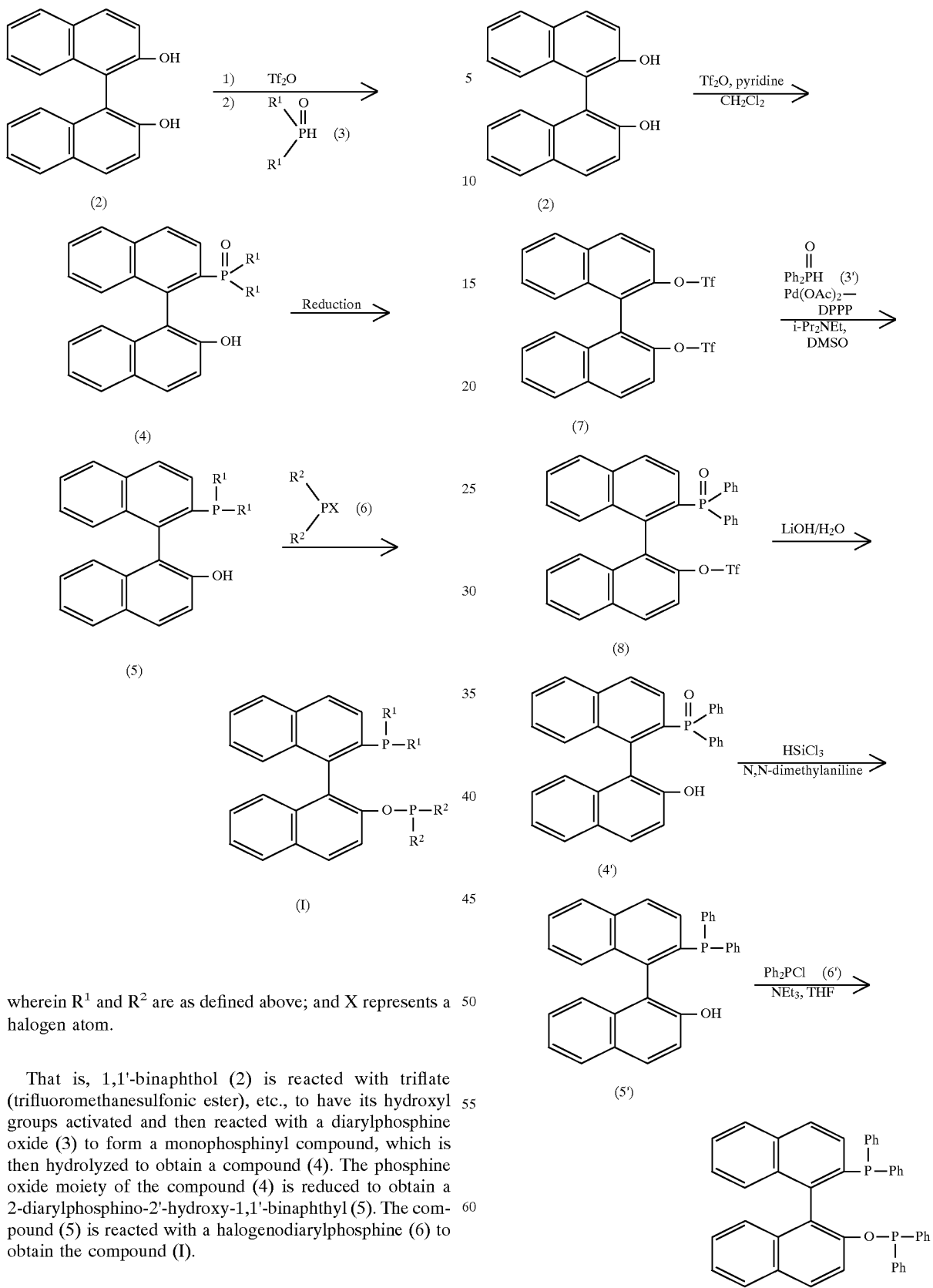

wherein R¹ and R² are as defined above; and X represents a halogen atom.

That is, 1,1'-binaphthol (2) is reacted with triflate (trifluoromethanesulfonic ester), etc., to have its hydroxyl groups activated and then reacted with a diarylphosphine oxide (3) to form a monophosphinyl compound, which is then hydrolyzed to obtain a compound (4). The phosphine oxide moiety of the compound (4) is reduced to obtain a 2-diarylphosphino-2'-hydroxy-1,1'-binaphthyl (5). The compound (5) is reacted with a halogenodiarylphosphine (6) to obtain the compound (I).

The above reaction steps will be explained in more detail, taking, for instance, a compound (I) in which both R¹ and R² are a phenyl group (represented by formula (I')).

wherein Tf represents a trifluoromethanesulfone group (CF$_3$SO$_2$—); Ph represents a phenyl group; Ac represents an acetyl group; DPPP represents 1,3-diphenylphosphinopropane; i-Pr represents an isopropyl group; Et represents an ethyl group; DMSO stands for dimethyl sulfoxide; and THF stands for tetrahydrofuran.

1,1'-Binaphthol (2) is reacted with trifluoromethanesulfonic acid anhydride (Tf2O) in methylene chloride in the presence of pyridine to obtain a ditriflate compound (7) according to the method described in *Tetrahedron Lett.*, Vol. 31, pp. 6321–6324 (1990). The ditriflate compound (7) is reacted with diphenylphosphine oxide (3') in dimethyl sulfoxide (DMSO) in the presence of palladium acetate, 1,3-diphenylphosphinopropane (DPPP), and diisopropylethylamine (i-Pr$_2$NEt) to obtain a monophosphinyl compound (8). The compound (8) is reacted in the presence of lithium hydroxide monohydrate (LiOH.H$_2$O) to hydrolyze the triflate moiety to give a compound (4'). The phosphine oxide moiety of the compound (4') is reduced in the presence of N,N-dimethylaniline and trichlorosilane (HSiCl$_3$) to give 2-diphenylphosphino-2'-hydroxy-1,1'-binaphthyl (5'), which is then reacted with chlorodiphenylphosphine (6') in the presence of triethylamine to obtain a phosphine-phosphinite compound (I') of the invention (a compound (I) wherein R$^1$=R$^2$=phenyl group).

In using (R)-1,1'-binaphthol as a starting material (2), a phosphine-phosphinite compound of the (R)-form is obtained. Starting with (S)-1,1'-binaphthol, a phosphine-phosphinite compound of the (S)-form is obtained.

Similarly, phosphine-phosphinite compound (I) wherein R$^1$ and/or R$^2$ is/are other than a phenyl group can be prepared by replacing the diarylphosphine oxide (3) and/or the halogenodiarylphosphine (6) accordingly.

In the phosphine-phosphinite compound (I) thus obtained, R$^1$ and R$^2$ may be either the same or different from each other and are independently selected from a phenyl group; a phenyl group substituted with a lower alkyl group, a lower alkoxy group, a phenyl group, a halogen atom, a halogen-substituted lower alkyl group, a lower alkyl-substituted phenyl group, a tri(lower alkyl)silyl group, a cyclopentyl group; a 3,4-methylenedioxy group or a 3,4-ethylenedioxy group; a naphthyl group, or a naphthyl group substituted with a lower alkyl group, a lower alkoxy group or a halogen atom. The naphthyl group includes a 1-naphthyl group and a 2-naphthyl group, with a 2-naphthyl group being preferred.

The lower alkyl group which may be on the phenyl or naphthyl group includes those having 1 to 4 carbon atoms, e.g., methyl, ethyl, propyl, isopropyl, and t-butyl groups, with a methyl group being preferred.

Examples of suitable (lower alkyl)-substituted phenyl groups are o-tolyl, m-tolyl, p-tolyl, 3,5-dimethylphenyl, mesityl, 3,5-di(t-butyl)phenyl, and 3,5-diethylphenyl, with 3,5-dimethylphenyl being preferred. Examples of suitable (lower alkyl)-substituted naphthyl groups are 6-methyl-2-naphthyl, 6-ethyl-2-naphthyl, and 6-t-butyl-2-naphthyl, with 6-methyl-2-naphthyl being preferred.

The lower alkoxy group which may be on the phenyl or naphthyl group includes those having 1 to 4 carbon atoms, such as methoxy, ethoxy, propyloxy, isopropyloxy, and t-butoxy groups. A methoxy group is preferred.

Examples of suitable (lower alkoxy)-substituted phenyl groups include p-methoxyphenyl, m-methoxyphenyl, and 3,5-dimethoxyphenyl. Examples of suitable (lower alkoxy)-substituted naphthyl groups are 6-methoxy-2-naphthyl, 6-ethoxy-2-naphthyl, and 6-t-butoxy-2-naphthyl. Preferred of them are 3,5-dimethoxyphenyl and 6-methoxy-2-naphthyl groups.

The halogen atom which may be on the phenyl or naphthyl group includes a fluorine atom, a chlorine atom, a bromine atom, and an iodine atom, with a fluorine atom being preferred.

Examples of suitable halogen-substituted phenyl groups include p-fluorophenyl, 3,5-difluorophenyl, p-chlorophenyl, 3,5-dichlorophenyl, p-bromophenyl, and 3,5-dibromophenyl. Examples of suitable halogen-substituted naphthyl groups include 6-fluoro-2-naphthyl, 6-chloro-2-naphthyl, and 6-bromo-2-naphthyl. Preferred are 3,5-difluorophenyl and 6-fluoro-2-naphthyl groups.

The halogen-substituted lower alkyl group which may be on the phenyl group includes a monofluoromethyl group, a difluoromethyl group, and a trifluoromethyl group, with a trifluoromethyl group being preferred. Examples of suitable phenyl groups substituted with the halogen-substituted lower alkyl group are p-trifluoromethylphenyl and 3,5-di(trifluoromethyl)phenyl, with 3,5-di(trifluoromethyl)phenyl being preferred.

The (lower alkyl)-substituted phenyl group which may be on the phenyl group includes o-tolyl, m-tolyl, p-tolyl, 3,5-dimethylphenyl, mesityl, 3,5-di(t-butyl)phenyl, 3,5-diethylphenyl, and 2,4,6-trimethylphenyl groups. A 3,5-dimethylphenyl group and a 2,4,6-trimethylphenyl group are preferred of them. Examples of suitable phenyl groups substituted with the (lower alkyl)-substituted phenyl group are p-(2,4,6-trimethylphenyl)phenyl, p-(3,5-dimethylphenyl)phenyl, and p-(2,4-dimethylphenyl)phenyl, with p-(3,5-dimethylphenyl)phenyl and p-(2,4,6-trimethylphenyl)phenyl being preferred.

The tri(lower alkyl)silyl group which may be on the phenyl group includes those having 1 to 4 carbon atoms in the lower alkyl moiety thereof, such as trimethylsilyl, triethylsilyl, triisopropylsilyl, and t-butyldimethylsilyl. A trimethylsilyl group is preferred. Examples of suitable phenyl groups substituted with the tri(lower alkyl)silyl group are 3,5-di(trimethylsilyl)phenyl, 3,5-di(t-butyldimethylsilyl)phenyl, and 3,5-di(triisopropylsilyl)phenyl, with 3,5-di(trimethylsilyl)phenyl being preferred.

Specific examples of preferred phosphine-phosphinite compounds (I) are listed in Table 1 below, in which preferred combinations of R$^1$ and R$^2$ are shown, only for illustrative purposes but not for limitation.

TABLE 1

| R$^1$ | R$^2$ |
|---|---|
| phenyl | phenyl |
| phenyl | p-tolyl |
| phenyl | p-fluorophenyl |
| phenyl | p-trifluoromethylphenyl |
| phenyl | 3,5-dimethylphenyl |
| phenyl | 3,5-difluorophenyl |
| phenyl | 3,5-di(trifluoromethyl)phenyl |
| 3,5-dimethylphenyl | phenyl |
| 2-naphthyl | phenyl |
| 2-naphthyl | p-fluorophenyl |
| 2-naphthyl | p-trifluoromethylphenyl |
| 2-naphthyl | 3,5-difluorophenyl |
| 6-methoxy-2-naphthyl | phenyl |
| 3-phenyl-phenyl | phenyl |
| 4-phenyl-phenyl | phenyl |
| 4-mesitylphenyl | phenyl |
| o-tolyl | phenyl |
| cyclohexyl | phenyl |
| 3,5-di(trimethylsilyl)-phenyl | phenyl |
| 3,4-methylenedioxyphenyl | phenyl |
| 3,4-methylenedioxyphenyl | p-fluorophenyl |
| 3,4-ethylenedioxyphenyl | phenyl |

TABLE 1-continued

| R¹ | R² |
|---|---|
| 3,4-ethylenedioxyphenyl | p-fluorophenyl |
| 3,5-dimethoxyphenyl | phenyl |
| 3,5-dimethoxyphenyl | p-fluorophenyl |
| 3,5-di-t-butylphenyl | phenyl |
| 3,5-di-t-butylphenyl | p-fluorophenyl |

Of the compounds shown in Table 1 above, those having a $R^1/R^2$ combination of 2-naphthyl/p-fluorophenyl, 2-naphthyl/p-trifluoromethylphenyl, and 2-naphthyl/3,5-difluorophenyl are particularly preferred.

The phosphine-phosphinite compound (I) of the invention is very useful as a catalyst component, especially for asymmetric hydroformylation. It can be used either in combination with a transition metal compound (typified by a compound of the group 8 metal of the Periodic Table) or in the form of a complex formed with the transition metal compound. The phosphine-phosphinite compound (I) to be used is selected from the (R)-form and the (S)-form in accordance with a desired steric configuration of the product.

Application of the phosphine-phosphinite compound (I) as a catalyst for asymmetric hydroformylation is described below taking, for instance, a hydroformylation reaction of a 4-vinylazetidin-2-one compound of formula (II) to prepare a 4-[(R)-1'-formylethyl]azetidin-2-one derivative, an important intermediate for medicines.

An optically active 4-[(R)-1'-formylethyl]azetidin-2-one derivative (III) can be prepared by hydroformylating a 4-vinylazetidin-2-one compound (II) in the presence of an (R)-form of the phosphine-phosphinite compound (I) (hereinafter referred to as an (R)-phosphine-phosphinite compound) and a rhodium compound with high selectivity and efficiency in accordance with the following reaction scheme:

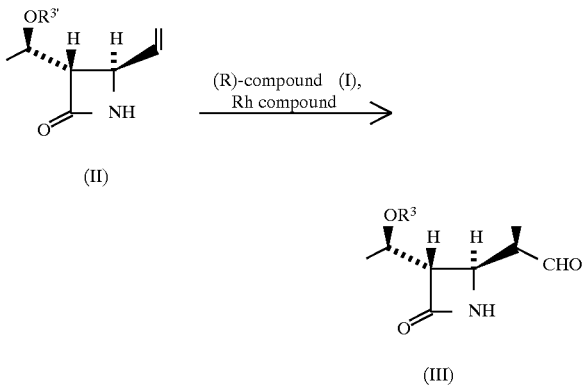

wherein $R^3$ is as defined above.

The starting compound, 4-vinylazetidin-2-one compound (II), can easily be synthesized by, for example, the process described, e.g., in *Liebing Ann. Chem.*, pp. 539–560 (1974) according to the following reaction scheme:

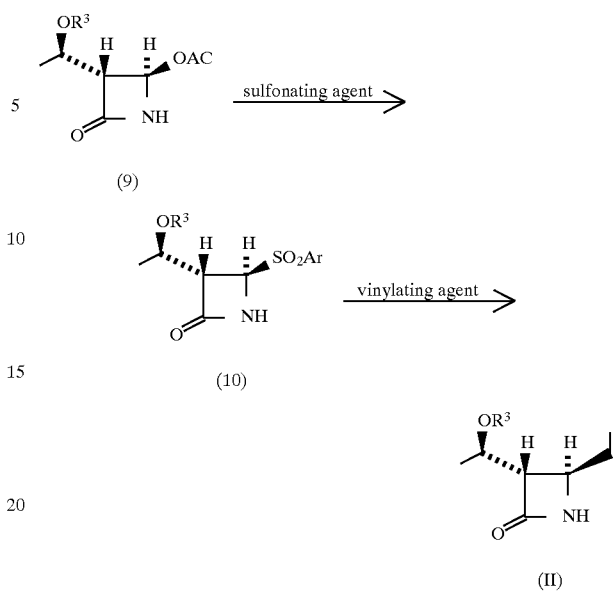

wherein $R^3$ is as defined above; and Ar represents a phenyl group which may be substituted with a halogen atom or a lower alkyl group.

A 4-acetoxyazetidin-2-one derivative (9) is reacted with sodium benzenesulfinate, sodium p-toluenesulfinate or a corresponding potassium or lithium salt thereof in a soluble solvent, such as acetone-water, methanol or water-methanol, to form a compound (10). The compound (10) is reacted with an organic vinyl compound, such as vinylmagnesium chloride, vinylmagnesium bromide, vinylmagnesium iodide, divinylmagnesium, vinyllithium, vinylzinc chloride, and divinylzinc, according to the process described in *J.C.S. Chem. Commn.*, pp. 736–738 (1980) to give the compound (II).

In the 4-vinylazetidin-2-one compound (II) thus prepared, $R^3$ represents a hydrogen atom or a protective group for a hydroxyl group. The protective group for a hydroxyl group as represented by $R^3$ is not particularly limited and is selected from generally used protective groups. Useful protective groups include a tri(lower alkyl)silyl group, a diphenyl(lower alkyl)silyl group, a triphenylsilyl group, a lower alkylcarbonyl group, a benzyl group, and a benzoyl group. A tri(lower alkyl)silyl group and a diphenyl(lower alkyl)silyl group are preferred.

The tri(lower alkyl)silyl group includes those having 1 to 6 carbon atoms in the alkyl moiety thereof, such as a t-butyldimethylsilyl group, a dimethylhexylsilyl group, a triethylsilyl group, a triisopropylsilyl group, and a trimethylsilyl group. Those having 1 to 4 carbon atoms in the alkyl moiety thereof are preferred. A t-butyldimethylsilyl group is still preferred. The diphenyl(lower alkyl)silyl group includes a t-butyldiphenylsilyl group.

The phosphine-phosphinite compound (I) which can be used as a ligand in the asymmetric hydroformylation includes those described above. In order to obtain a 4-[(R)-1'-formylethyl]azetidin-2-one derivative (III), it is necessary to use a phosphine-phosphinite compound having an (R)-configuration.

In carrying out the asymmetric hydroformylation, the (R)-phosphine-phosphinite compound (I) is used in an amount of 0.0005 to 10 mol %, preferably 0.001 to 5 mol %, based on the substrate, 4-vinylazetidin-2-one compound (II).

The rhodium compound, which is the other catalyst component, is not particularly limited. Any rhodium compound that can form a complex with the (R)-phosphine-phosphinite compound (I) can be used. Useful rhodium compounds include those represented by formulae (IV) to (VI):

| [Rh(L)X]$_2$ | (IV) |
| [Rh(M) (acac)] | (V) |
| [Rh(CO)$_2$Y]$_2$ | (VI) | wherein L represents 1,5-cyclooctadiene (hereinafter abbreviated to COD) or norbornadiene (hereinafter abbreviated to NBD); X represents a halogen atom or an acetyloxy group; "acac" represents acetylacetonato; M represents COD, NBD or (CO)$_2$; and Y represents a halogen atom.

Of the rhodium compounds (IV) to (VI), those of formula (IV) are particularly preferred. Specific examples of the compounds (IV) are [Rh(COD)Cl]$_2$, [Rh(COD)Br]$_2$, [Rh(COD)I]$_2$, [Rh(COD)OAc]$_2$ (Ac: acetyl group), [Rh(NBD)Cl]$_2$, [Rh(NBD)Br]$_2$, [Rh(NBD)I]$_2$, and [Rh(NBD)OAc]$_2$. [Rh(COD)Cl]$_2$ is particularly preferred.

Specific examples of the compounds (V), [Rh(M)(acac)], are [Rh(COD)(acac)), [Rh(NBD)(acac)], and (Rh(CO)$_2$(acac)], with [Rh(CO)$_2$(acac)] being preferred.

Specific examples of the compounds (VI), [Rh(CO)$_2$Y]$_2$, include [Rh(CO)$_2$Cl]$_2$, [Rh(CO)$_2$Br]$_2$, and [Rh(Co)$_2$I]$_2$, with [Rh(CO)$_2$Cl]$_2$ being preferred.

The rhodium compound is used in an amount of from ¼ mol to equimole, preferably form ⅓ to ½ mol, per mole of the phosphine-phosphinite compound.

Any kind of solvents can be used in the reaction system as far as no adverse influence is given to the reaction. Preferred are hydrocarbon solvents, such as hexane, heptane, octane, isooctane, nonane, decane, cyclohexane, cyclopentane, benzene, toluene, xylene, and mesitylene. Additionally, ethers, such as diisopropyl ether, dibutyl ether, tetrahydrofuran, dimethoxyethane, and diethylene glycol dimethyl ether; ketones, such as acetone and methyl ethyl ketone; and esters, such as ethyl acetate, butyl lactate, and butyl benzoate, are also useful. These solvents may be used either individually or as a mixture of two or more thereof.

In general, presence of water in a hydroformylation reaction system is preferred for the purpose of increasing the catalytic activity. The hydroformylation reaction according to the present invention can also be carried out in the copresence of water. While the amount of water to be added is not particularly limited, an extremely small amount of water produces little effect, and addition of an extremely large amount of water does not pay. Accordingly, the amount of water that would bring about a substantial increase in reaction rate is 0.001 to 1, preferably 0.01 to 0.1, in terms of weight ratio to the substrate.

If desired, various additives in addition to water may be added to the reaction system for the purpose of improving the catalytic activity, regioselectivity, and diastereoselectivity. Such additives include phosphorus compounds, such as a trialkylphosphine oxide (e.g., triethylphosphine oxide or tributylphosphine oxide), triphenylphosphine oxide, a trialkyl phosphite (e.g., triethyl phosphite or tributyl phosphite), and triphenyl phosphite; and carboxylic acids, such as acetic acid, propionic acid, and pivalic acid. These additives can be added in an amount of 1 to 10 mols, preferably 2 to 4 mols, per mole of the rhodium compound.

The hydroformylation reaction is carried out at a temperature of −200° to 250° C., preferably 10° to 150° C. Within this range, a lower temperature is advantageous for the heat stability of the aldehyde produced, while a higher temperature is desirable for the reaction rate. The reaction time is from 1 to 48 hours, preferably 6 to 15 hours.

The reaction is conducted in the presence of carbon monoxide and hydrogen as in general hydroformylation reactions. The reaction pressure is 5 to 200 atm, preferably 20 to 150 atm. A mixing molar ratio of carbon monoxide to hydrogen is 10 to 0.1, preferably 4 to 0.25. As far as the carbon monoxide to hydrogen molar ratio falls within this range, the gas phase may be diluted with other inert gases, such as methane, nitrogen, argon, helium, carbon dioxide, and mixtures thereof.

As stated above, the reaction is carried out in the presence of the phosphine-phosphinite compound (I) of R-form and a rhodium compound. It is possible to perform the reaction in the presence of a previously prepared complex of the (R)-phosphine-phosphinite compound (I) and the rhodium compound. In other words, the effects exerted in the reaction system are equal irrespective of whether the (R)-phosphine-phosphinite compound (I) and a rhodium compound are added individually or in the form of a complex thereof.

A complex of the (R)-phosphine-phosphinite compound (I) and a rhodium compound can easily be prepared by reacting them at an (R)-phosphine-phosphinite compound to rhodium compound molar ratio of 1:1 to 4:1 in an appropriate solvent, such as methylene chloride, toluene, benzene, hexane, and pentane, at a temperature of 10° to 25° C.

Where the reaction is performed using the complex, the complex is added in an amount of 0.0005 to 10 mol %, preferably 0.001 to 5 mol %, based on the substrate. Other reaction conditions are the same as described above.

The hydroformylation reaction using the (R)-phosphine-phosphinite compound (I) hardly produces problematical by-products, such as the n-form and α-form, which had accompanied conventional hydroformylation techniques and thereby achieve synthesis of a desired β-form at a high selectivity of about 70% in terms of a β-form to n-form production ratio.

The thus prepared 4-[(R)-1'-formylethyl]azetidin-2-one derivative (III) is a useful intermediate, which is oxidized in a conventional manner, for example, by Jones oxidation, to convert its formyl group to a carboxyl group and ultimately led to carbapenem antibiotics.

The present invention will now be illustrated in greater detail with reference to Examples, but it should be understood that the invention is not deemed to be limited thereto. Unless otherwise indicated, all the percents are by weight.

Measurement of nuclear magnetic resonance (NMR) spectrum and high-performance liquid chromatography (HPLC) were carried with the following equipment.

NMR Analysis:
AM-400 (400 MHz, manufactured by Bruker Inc.)
Internal standard: $^1$H-NMR: tetramethylsilane
$^{31}$P-NMR: 85% phosphoric acid
HPLC:
Hitachi L-6000, manufactured by Hitachi, Ltd.

EXAMPLE 1

Synthesis of (R)-2-Di(3,5-dimethylphenyl)-phosphino-2'-diphenylphosphinoxy-1,1'-binaphthalene (1) Synthesis of Di(3,5-dimethylphenyl)phosphine Oxide:
In a 500 ml four-necked flask equipped with a dropping funnel, a reflux condenser, and a thermometer was put 6.57 g (0.270 mol) of magnesium. After purging with nitrogen, 20 ml of tetrahydrofuran was added, and small amounts of iodine and 1,2-dibromoethane were added thereto to activate magnesium. A solution of 50.00 g (0.270 mol) of 5-bromo-m-xylene in 160 ml of tetrahydrofuran was added thereto dropwise at 25° to 30° C. over 1.5 hours, followed by stirring at 40° C. for 30 minutes. A solution of 12.44 g (0.090 mol) of diethyl phosphite in 15 ml of tetrahydrofuran was added dropwise to the mixture at 25° to 30° C., and the reaction mixture was stirred at room temperature for 15 hours.

After completion of the reaction, the reaction mixture was poured into a solution of 37.34 g (0.270 mol) of potassium carbonate in 46 ml of water at 0° C., stirred at room temperature for 30 minutes, and filtered. The filter cake was washed with two 150 ml portions of ethanol, and the washing was combined with the filtrate. The filtrate was evaporated under reduced pressure to remove the solvent, and to the residue were added 200 ml of chloroform and Molecular Sieve 4A. After stirring for 2 hours, the solid was filtered off, and the filtrate was evaporated under reduced pressure to remove the solvent to give 17.70 g (yield: 76%) of the title compound as white crystals.

$^{31}$P-NMR (400 MHz, CDCl$_3$, δ, ppm): 24.9 (d, J=498Hz)

(2) Synthesis of (R)-2,2'-Bis(trifluoromethanesulfonyloxy)-1,1'-binaphthyl:

To a suspension of 115.32 g (0.403 mol) of (R)-1,1'-bi-2-naphthol in 600 ml of methylene chloride was added 79.6 g (1.01 mol) of pyridine at room temperature in a nitrogen stream. To the solution was added dropwise 250.00 g (0.886 mol) of trifluoromethanesulfonic acid anhydride at 0 to 5° C., followed by stirring at room temperature for 15 hours. After completion of the reaction, the solvent was removed by evaporation under reduced pressure, and the residue was added to a mixture of 1250 ml of a 5% aqueous solution of hydrochloric acid and 1800 ml of diethyl ether. The mixture was stirred for 30 minutes and allowed to stand for liquid-liquid separation. The aqueous layer was extracted with two 500 ml portions of diethyl ether, and the resulting organic layer was washed successively with two 1000 ml portions of water and 1000 ml of a saturated sodium chloride aqueous solution, dried over magnesium sulfate, and evaporated under reduced pressure to remove the solvent. Recrystallization of the residue from hexane gave 216.35 g (yield: 98%) of the title compound.

(3) Synthesis of (R)-2-Di(3,5-dimethylphenyl)phosphinyl-2'-trifluoromethanesulfonyloxy-1,1'-binaphthyl:

In a 100 ml three-necked flask equipped with a reflux condenser and a thermometer were charged 5.00 g (9.08 mmol) of (R)-2,2'-bis(trifluoromethanesulfonyloxy)-1,1'-binaphthyl, 3.05 g (11.81 mmol) of di(3,5-dimethylphenyl)phosphine oxide, 203.9 mg (0.908 mmol) of palladium acetate, and 374.6 mg (0.908 mmol) of 1,3-diphenylphosphinopropane. After purging the flask with nitrogen, 50 ml of dimethyl sulfoxide was added, and the mixture was stirred at room temperature for 15 minutes. To the reaction mixture was added 2.35 g (18.17 mmol) of diisopropylethylamine, followed by heating at 100° C. for 15 hours while stirring.

After completion of the reaction, the reaction mixture was poured into a mixture of 100 ml of diethyl ether and 100 ml of a 5% hydrochloric acid aqueous solution, stirred for 1.5 hours, and allowed to stand for liquid-liquid separation. The aqueous layer was extracted with two 100 ml portions of diethyl ether, and the resulting organic layer was washed successively with two 100 ml portions of water and 100 ml of a saturated sodium chloride aqueous solution, dried over magnesium sulfate, and evaporated under reduced pressure to remove the solvent. The residue was purified by silica gel column chromatography using a mixture of hexane and ethyl acetate (2/1 to 1/1 by volume) as a developing solvent to give 5.02 g (yield: 84%) of the title compound.

$^{31}$P-NMR (400 MHz, CDCl$_3$, δ, ppm): 29.5 (m)

(4) Synthesis of (R)-2-Di(3,5-dimethylphenyl)phosphinyl-2'-hydroxy-1,1'-binaphthyl:

In a 100 ml flask, 5.00 g (7.59 mmol) of (R)-2-di(3,5-dimethylphenyl)phosphinyl-2'-trifluoromethanesulfonyloxy-1,1'-binaphthyl was dissolved in 45 ml of tetrahydrofuran, and 15 ml of water and 1.60 g (37.96 mmol) of lithium hydroxide monohydrate were added thereto, followed by stirring at room temperature for 15 hours. The solvent was removed by evaporation. To the residue were added 20 ml of toluene and 40 ml of a 5% hydrochloric acid aqueous solution. After stirring for 30 minutes, the precipitated solid was collected by filtration to obtain 3.10 g (yield: 78%) of the title compound.

$^{31}$P-NMR (400 MHz, CDCl$_3$, δ, ppm): 31.2 (m)

(5) Synthesis of (R)-2-Di(3,5-dimethylphenyl)phosphino-2'-hydroxy-1,1'-binaphthyl:

In a 100 ml three-necked flask equipped with a reflux condenser and a thermometer was charged a solution of 800 mg (5.70 mmol) of(R)-2-di(3,5-dimethylphenyl)phosphinyl-2'-hydroxy-1,1'-binaphthyl in 16 ml of toluene, and 1.62 g (13.37 mmol) of N,N'-dimethylaniline and 1.65 g (12.15 mmol) of trichlorosilane were added thereto at room temperature in a nitrogen stream. The resulting mixture was stirred at 100° C. for 17 hours.

After completion of the reaction, the reaction mixture was allowed to cool to room temperature, and 20 ml of a 25% aqueous solution of sodium hydroxide was added thereto carefully. After stirring at room temperature for 1 hour, the reaction mixture was allowed to stand for liquid-liquid separation. The aqueous layer was extracted with two 20 ml portions of diethyl ether, and the resulting organic layer was washed successively with two 50 ml portions of a 5% hydrochloric acid aqueous solution, two 50 ml portions of water, and 50 ml of a saturated sodium chloride aqueous solution, dried over magnesium sulfate, and evaporated to remove the solvent. The residue was purified by silica gel column chromatography using benzene as a developing solvent to give 670 mg (yield: 86%) of the title compound.

$^{31}$P-NMR (400 MHz, CDCl$_3$, δ, ppm): −11.8 (m)

(6) Synthesis of (R)-2-Di(3,5-dimethylphenyl)phosphino-2'-diphenylphosphinoxy-1,1'-binaphthyl:

In a 30 ml flask was charged a solution of 500 mg (0.979 mmol) of (R)-2-di(3,5-dimethylphenyl)phosphino-2'-hydroxy-1,1'-binaphthyl in 5 ml of tetrahydrofuran, and 108.9 mg (1.077 mmol) of triethylamine was added thereto, followed by stirring for 15 minutes. Then, 237.7 mg (1.077 mmol) of chlorodiphenylphosphine was added at 0° C., and the mixture was stirred at room temperature for 1 hour. After completion of the reaction, the solvent was removed by evaporation, and the residue was purified by silica gel column chromatography using a mixture of benzene and diethyl ether (5/1 by volume) as a developing solvent to give 670 mg (yield: 99%) of the title compound.

$^{31}$P-NMR (400 MHz, CDCl$_3$, δ, ppm):
−12.0 (m), 111.4 (d, J=7Hz)

EXAMPLES 2 TO 21

Phosphine-phosphinite compounds (I) shown in Table 2 below were synthesized in the same manner as in Example 1, except for replacing the di(3,5-dimethylphenyl)phosphine oxide used in Example 1-(3) with compounds represented by formula: $R^1_2P(O)H$ ($R^1$ is shown in Table 2) and replacing the chlorodiphenylphosphine used in Example 1-(6) with compounds represented by formula: $R^2_2PCl$ ($R^2$ is shown in Table 2). In Table 2, the resulting phosphine-phosphinite compounds (I) are shown by $R^1$ and $R^2$. The NMR spectral data of the compounds obtained are also shown in Table 2.

TABLE 2

| Example | R¹ | R² | $^{31}$P-NMR (400 MHz, CDCl$_3$, δ ppm) |
|---|---|---|---|
| 2 | phenyl | phenyl | −13.0(d, J=6Hz), 111.3(d, J=6Hz) |
| 3 | phenyl | 4-CH$_3$-phenyl | −13.0(m), 112.4(m) |
| 4 | phenyl | 4-F-phenyl | −13.2(m), 110.4(m) |
| 5 | phenyl | 4-CF$_3$-phenyl | −13.2(m), 106.7(m) |
| 6 | phenyl | 3,5-dimethylphenyl | −12.7(m), 111.4(m) |
| 7 | phenyl | 3,5-difluorophenyl | −13.2(m), 106.2(m) |
| 8 | phenyl | 3,5-bis(CF$_3$)phenyl | −13.1(d, J=6Hz), 101.8(m) |
| 9 | 2-naphthyl | phenyl | −11.7(m), 112.1(m) |
| 10 | 2-naphthyl | 4-F-phenyl | −12.1(m), 111.2(d, J=4Hz) |
| 11 | 2-naphthyl | 4-CF$_3$-phenyl | −12.2(m), 107.4(m) |

TABLE 2-continued
| Example | R¹ | R² | ³¹P-NMR (400 MHz, CDCl₃, δ ppm) |
|---|---|---|---|
| 12 | 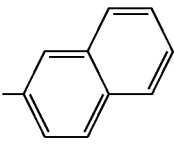 | 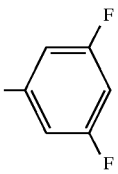 | −11.7(d, J=7Hz), 105.6(m) |
| 13 | 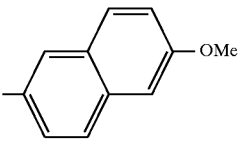 | 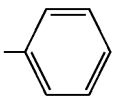 | −12.4(d, J=7Hz), 111.7(d, J=7Hz) |
| 14 | 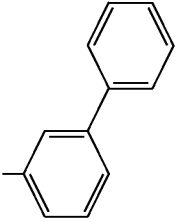 |  | −12.0(m), 111.9(m) |
| 15 | 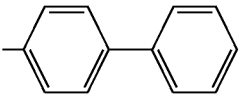 |  | −13.0(m), 111.0(m) |
| 16 | 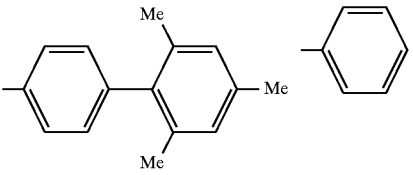 |  | −12.8(m), 112.2(m) |
| 17 | 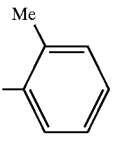 |  | −12.0(m), 112.1(m) |
| 18 | 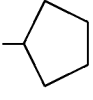 | 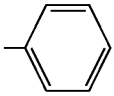 | −9.8(m), 113.0(m) |
| 19 | 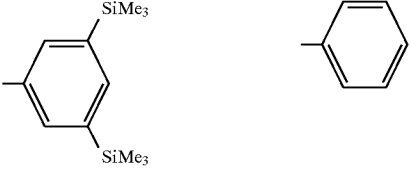 | 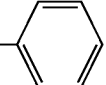 | −13.7(d, J=7Hz), 111.8(br) |
| 20 | 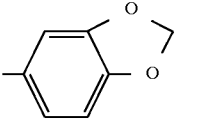 | 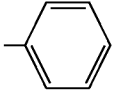 | −10.2(m), 110.6(m) |
| 21 | 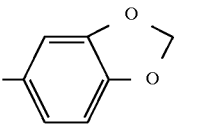 | 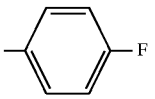 | −10.5(d, J=6Hz), 109.7(d, J=6Hz) |

EXAMPLE 22

Synthesis of (3S,4R)-3-((R)-1-t-Butyldimethyl-silyloxy)ethyl-4-((R)-1'-formylethyl)azetidin-2-one In a 100 ml autoclave were charged 1.9 mg (7.8 μmol) of [Rh(COD)Cl]$_2$, 13.6 mg (19.58 μmol) of (R)-2-di(3,5-dimethylphenyl)phosphino-2'-diphenylphosphinoxy-1,1'-binaphthyl, and 1.00 g (3.92 mmol) of (1R,3S,4R)-vinylazetidin-2-one. After thoroughly purging the autoclave with nitrogen, 2 ml of n-decane was added. To the autoclave was fed carbon monoxide to an inner pressure of 25 atm, and hydrogen was then introduced therein to a total inner pressure of 50 atm. The autoclave was heated to 60° C. in a water bath, at which the mixture was kept under vigorous stirring for 48 hours. After allowing the reaction mixture to cool to room temperature, excess carbon monoxide and hydrogen were discharged.

HPLC Analysis of the reaction solution revealed that (3S,4R)-3-((R)-1-t-butyldimethylsilyloxy)ethyl-4-((R)-1'-formylethyl)azetidin-2-one (β-form), (3S,4R)-3-((R)-1-t-butyldimethylsilyloxy)ethyl-4-((S)-1'-formylethyl)azetidin-2-one (α-form), and (3S,4R)-3-((R)-1-t-butyldimethylsilyloxy)ethyl-4-(2-formylethyl)-azetidin-2-one (n-form) had been produced at a β-form/α-form selectivity ratio of 95/5, a (β-form+α-form)/n-form selectivity ratio of 72/28, i.e., a β-form/α-form/n-form selectivity ratio of 68.4/3.6/28.

The reaction mixture was evaporated under reduced pressure to remove n-decane, and the residue was purified by silica gel column chromatography to obtain 765 mg (yield: 68%) of a mixture of I-form and a-form (β-form/α-form=95/5).

The selectivity ratios as above referred to were decided from the integral ratio of the aldehyde proton in the $^1$H-NMR spectrum and the results of HPLC (Cosmosil 5C18-MS; eluent: acetonitrile/water=65/35; flow rate: 0.5 ml/min; detector: Shodex RI SE-51). β-Form:

$^1$H-NMR (400 MHz, CDCl$_3$, δ, ppm):
0.07 (s, 3H), 0.08 (s, 3H), 0.88 (s, 9H), 1.22 (d, J=7.3Hz, 3H), 1.24 (d, J=6.3Hz), 2.68 (m, 1H), 3.94 (dd, J=5.4, 2.4Hz, 1H), 4.20 (m, 1H), 5.98 (s, 1H), 9.81 (d, J=1.1 Hz, 1H)

COMPARATIVE EXAMPLES 1 TO 3

A hydroformylation reaction was carried out in the same manner as in Example 22, except for replacing (R)-2-di(3,5-dimethylphenyl)phosphino-2'-diphenylphosphinoxy-1,1'-binaphthyl with phosphine compound (A), (B) or (C) shown below. The production ratios of the β-form, α-form, and n-form are shown in Table 3 below.

TABLE 3

Compound A:

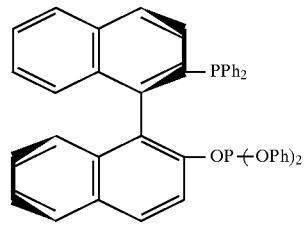

Compound B:

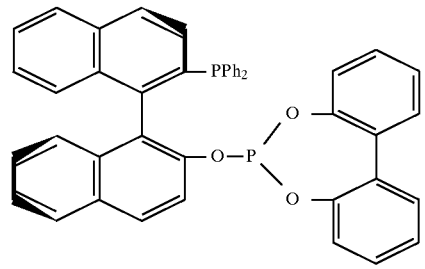

Compound C:

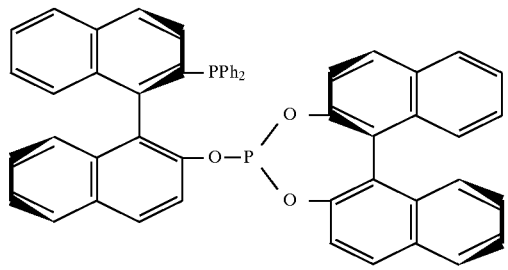

| | Phosphine Compound | Ratio 1[1] | Ratio 2[2] | Ratio 3[3] | Yield[4] |
|---|---|---|---|---|---|
| Comparative | Compound A | 67/33 | 60/40 | 40/20/40 | —[5] |

TABLE 3-continued

| Example 1 | | | | | |
|---|---|---|---|---|---|
| Comparative Example 2 | Compound B | 85/15 | 53/47 | 45/8/47 | —[5] |
| Comparative Example 3 | Compound C | 94/6 | 55/45 | 51.7/3.3/45 | 35% |
| Example 22 | (R)-2-Di(3,5-dimethyl-phenyl)phosphino-2'-dimethylphosphinoxy-1,1'-binaphthalene | 95/5 | 72/28 | 68.4/3.6/28 | 68% |

Note
1): β-Form/α-form ratio
2): (β-Form + α-form)/n-form ratio
3): β-Form/α-form/n-form ratio
4): Yield of (β-form + α-form)
5): The purification step (recrystallization) scarcely yielded crystals.

As is seen from Table 3, Example 22 shows improvement in both (β-form+α-form)/n-form ratio and β-form/α-form ratio over every Comparative Example. As a result, the proportion of the β-form in the β-form/α-form/α-form ratio in Comparative Examples is about 50 or lower, whereas that attained in Example 22 is 68.4, showing a marked improvement. Besides the selectivity, Example 22 achieves double the yield of Comparative Example 2.

The phosphine-phosphinite compound of the invention was thus proved to be a specifically effective catalyst for selective hydroformylation of a 4-vinylazetidin-2-one compound (II).

EXAMPLES 23 TO 42

A hydroformylation reaction was carried out in the same manner as in Example 22, except for replacing (R)-2-di(3,5-dimethylphenyl)phosphino-2'-diphenylphosphinoxy-1,1'-binaphthyl with each of the phosphine-phosphinite compounds shown in Table 4 below, replacing [Rh(COD)Cl]$_2$ with each of the rhodium compounds shown in the table, and making alterations in solvent, substrate/Rh compound molar ratio (S/C), ligand/Rh compound molar ratio (L/Rh), and reaction time as shown in the table. The reaction results are also shown in the table. In Table 4, Me stands for a methyl group.

TABLE 4

| Example No. | Phosphine-Phosphinite Compound I | | Rh Compound | Solvent | S/C | L/Rh | Time (hr) | Conversion (%) | β/α | Yield (%) |
|---|---|---|---|---|---|---|---|---|---|---|
| | R[1] | R[2] | | | | | | | | |
| 23 | 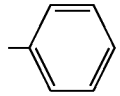 | 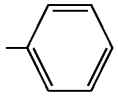 | Rh(CO)$_2$(acac) | acetone | 1000 | 5 | 6 | 20 | 95/5 | 58 |
| 24 | 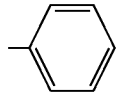 | 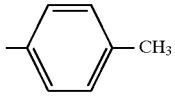 —CH$_3$ | [Rh(COD)Cl]$_2$ | acetone | 500 | 5 | 6 | 38 | 95/5 | 53 |
| 25 | 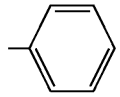 |  —F | [Rh(COD)Cl]$_2$ | n-decane | 500 | 5 | 6 | 65 | 95/5 | 64 |
| 26 | 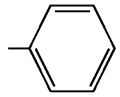 | 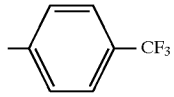 —CF$_3$ | [Rh(COD)Cl]$_2$ | acetone | 500 | 5 | 6 | 82 | 88/12 | 51 |
| 27 | 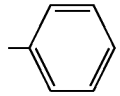 | 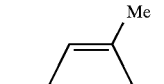 Me, Me | Rh(CO)$_2$(acac) | acetone | 1000 | 5 | 6 | 37 | 94/6 | 50 |

TABLE 4-continued

| Example No. | Phosphine-Phosphinite Compound I R¹ | R² | Rh Compound | Solvent | S/C | L/Rh | Time (hr) | Conversion (%) | β/α | Yield (%) |
|---|---|---|---|---|---|---|---|---|---|---|
| 28 | phenyl | 3,5-difluorophenyl | Rh(CO)₂(acac) | benzene | 1000 | 5 | 15 | 100 | 75/25 | 48 |
| 29 | phenyl | 3,5-bis(trifluoromethyl)phenyl | Rh(CO)₂(acac) | benzene | 1000 | 5 | 15 | 92 | 54/46 | 31 |
| 30 | 2-naphthyl | phenyl | [Rh(COD)Cl]₂ | benzene | 500 | 2.5 | 6 | 54 | 94/6 | 67 |
| 31 | 2-naphthyl | 4-fluorophenyl | [Rh(COD)Cl]₂ | n-decane | 500 | 2.5 | 6 | 86 | 95/5 | 67 |
| 32 | 2-naphthyl | 4-(trifluoromethyl)phenyl | [Rh(COD)Cl]₂ | n-decane | 500 | 2.5 | 6 | 94 | 95/5 | 70 |
| 33 | 2-naphthyl | 3,5-difluorophenyl | [Rh(COD)Cl]₂ | n-decane | 500 | 2.5 | 6 | 96 | 93/7 | 67 |
| 34 | 6-methoxy-2-naphthyl | phenyl | [Rh(COD)Cl]₂ | benzene | 500 | 2.5 | 6 | 47 | 94/6 | 67 |
| 35 | 3-biphenylyl | phenyl | [Rh(COD)Cl]₂ | benzene | 500 | 5 | 6 | 32 | 93/7 | 60 |
| 36 | 4-biphenylyl | phenyl | [Rh(COD)Cl]₂ | benzene | 500 | 5 | 6 | 67 | 93/7 | 60 |

TABLE 4-continued

| Example No. | Phosphine-Phosphinite Compound I R¹ | R² | Rh Compound | Solvent | S/C | L/Rh | Time (hr) | Conversion (%) | β/α | Yield (%) |
|---|---|---|---|---|---|---|---|---|---|---|
| 37 | 2,4,6-trimethylbiphenyl | phenyl | [Rh(COD)Cl]₂ | n-decane | 500 | 5 | 6 | 65 | 93/7 | 59 |
| 38 | o-tolyl | phenyl | [Rh(COD)Cl]₂ | benzene | 500 | 5 | 6 | 23 | 52/48 | 33 |
| 39 | cyclopentyl | phenyl | Rh(CO)₂(acac) | n-decane | 500 | 5 | 6 | 6 | 82/28 | 67 |
| 40 | 3,5-bis(SiMe₃)phenyl | phenyl | [Rh(COD)Cl]₂ | benzene | 500 | 5 | 6 | 33 | 93/7 | 56 |
| 41 | 3,4-methylenedioxyphenyl | phenyl | [Rh(COD)Cl]₂ | n-decane | 500 | 2.5 | 6 | 46 | 92/8 | 60 |
| 42 | 3,4-methylenedioxyphenyl | 4-F-phenyl | [Rh(COD)Cl]₂ | n-decane | 500 | 2.5 | 6 | 78 | 93/7 | 60 |

Note:
S/C: Substrate to Rh compound molar ratio
L/Rh: Ligand to Rh compound molar ratio As has been fully described and demonstrated, the novel phosphine-phosphinite compound (I) according to the invention is a very useful catalyst for asymmetric hydroformylation, which is used in combination with a transition metal compound or in the form of a complex with the transition metal compound. By using the phosphine-phosphinite compound (I) as a catalyst, an important intermediate for carbapenem antibiotics or a precursor thereof can be synthesized with ease at high regioselectivity and high diastereo-selectivity.

While the invention has been described in detail and with reference to specific examples thereof, it will be apparent to one skilled in the art that various changes and modifications can be made therein without departing from the spirit and scope thereof.

What is claimed is:

1. A phosphine-phosphinite compound represented by formula (I):

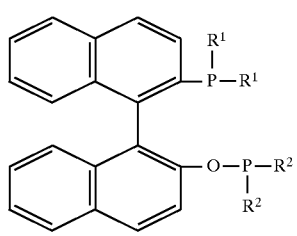

wherein $R^1$ and $R^2$, which may be the same or different, each represent a phenyl group; a phenyl group substituted with a lower alkyl group, a lower alkoxy group, a phenyl group, a halogen atom, a halogen-substituted lower alkyl group, a lower alkyl-substituted phenyl group, a tri(lower alkyl)silyl group, a cyclopentyl group, a 3,4-methylenedioxy group, or a 3,4-ethylenedioxy ground; a naphthyl group; a naphthyl group substituted with a lower alkyl group, a lower alkoxy group, or a halogen atom; or a cyclopentyl or cyclohexyl group.

2. A process for preparing a 4-[(R)-1'-formylethyl] azetidin-2-one represented by formula (III):

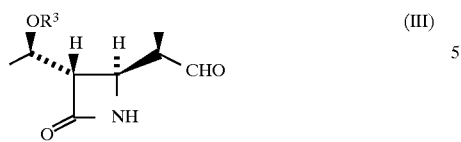

wherein $R^3$ represents a hydrogen atom or a protective group for a hydroxyl group,
which comprises hydroformylating a 4-vinylazetidin-2-one compound represented by formula (II):

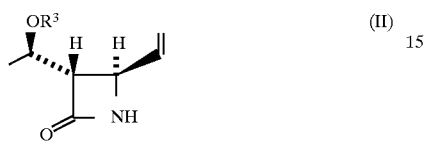

wherein $R^3$ is as defined above, in the presence of the (R)-form of a phosphine-phosphinite compound represented by formula (I):

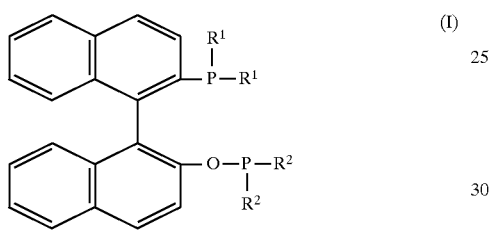

wherein $R^1$ and $R^2$, which may be the same or different, each represent a phenyl group; a phenyl group substituted with a lower alkyl group, a lower alkoxy group, a phenyl group, a halogen atom, a halogen-substituted lower alkyl group, a lower alkyl-substituted phenyl group, a tri(lower alkyl)silyl group, a cyclopentyl group, a 3,4-methylenedioxy groups or a 3,4-ethylenedioxy group; a naphthyl group; a naphthyl group substituted with a lower alkyl group, a lower alkoxy group, or a halogen atom; or a cyclopentyl or cyclohexyl group and in the presence of a rhodium compound.

3. A process for preparing a 4-[(R)-1'-formylethyl] azetidin-2-one represented by formula (III):

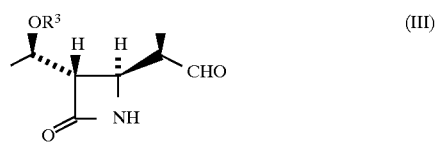

wherein $R^3$ represents a hydrogen atom or a protective group for a hydroxyl group, which comprises hydroformylating a 4-vinylazetidin-2-one compound represented by formula (II):

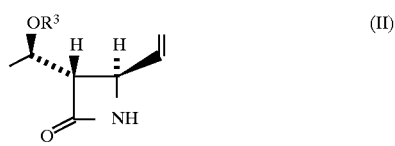

wherein $R^3$ is as defined above, in the presence of a complex with a rhodium compound comprising the (R)-form of a phosphine-phosphinite compound represented by formula (I):

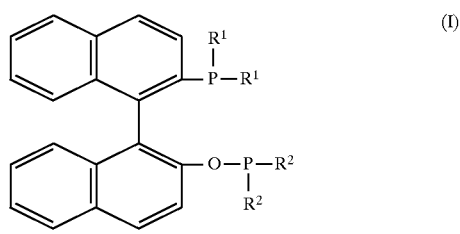

wherein $R^1$ and $R^2$, which may be the same or different, each represent a phenyl group; a phenyl group substituted with a lower alkyl group, a lower alkoxy group, a phenyl group, a halogen atom, a halogen-substituted lower alkyl group, a lower alkyl-substituted phenyl group, a tri(lower alkyl)silyl group, a cyclopentyl group, a 3,4-methylenedioxy group, or a 3,4-ethylenedioxy group; a naphthyl group; a naphthyl group substituted with a lower alkyl group, a lower alkoxy group or a halogen atom; or a cylcopentyl or cyclohexyl group.

* * * * *